United States Patent [19]

Sakuma et al.

[11] Patent Number: 5,112,136
[45] Date of Patent: May 12, 1992

[54] METHOD OF AND APPARATUS FOR MEASURING THERMAL CONDUCTIVITY

[76] Inventors: Kiyoshi Sakuma; Masayoshi Kaji, both c/o Nippon Steel Chemical Co., Ltd., 13-16, Ginza 5-chome, Chuo-ku, Tokyo, Japan

[21] Appl. No.: 587,121

[22] Filed: Sep. 24, 1990

[51] Int. Cl.$^5$ .......................................... G01N 25/018
[52] U.S. Cl. ..................................... 374/44; 374/10
[58] Field of Search ...................... 374/10, 29, 30, 31, 374/33, 43, 44

[56] References Cited

U.S. PATENT DOCUMENTS

| | | | |
|---|---|---|---|
| 1,680,638 | 8/1928 | Rowan | 374/10 |
| 2,342,029 | 2/1944 | Zubko | 374/44 X |
| 2,878,669 | 3/1959 | Knudson et al. | 374/44 |
| 3,045,473 | 7/1962 | Hager, Jr. | 374/44 |
| 3,981,175 | 9/1976 | Hammond, III et al. | 374/10 |
| 4,246,785 | 1/1981 | Sellers et al. | 374/43 |
| 4,568,198 | 2/1986 | Szabó et al. | 374/43 |
| 4,653,934 | 3/1987 | Pursley | 374/31 |
| 4,859,078 | 8/1989 | Bowman et al. | 374/44 |
| 4,978,230 | 12/1990 | Adiutori et al. | 374/43 |

FOREIGN PATENT DOCUMENTS

| | | | |
|---|---|---|---|
| 1179186 | 9/1985 | U.S.S.R. | 374/44 |
| 1476364 | 4/1989 | U.S.S.R. | 374/44 |

Primary Examiner—William A. Cuchlinski, Jr.
Assistant Examiner—G. Bradley Bennett
Attorney, Agent, or Firm—Armstrong, Nikadio, Marmelstein, Kubovcik & Murray

[57] ABSTRACT

A method and apparatus measures thermal conductivity of a material effected by measuring a change in the temperature of the material in contact with a heat source maintained at a predetermined temperature. A temperature change characteristic is obtained from the result of the temperature measurement, and the thermal conductivity is obtained by comparison of the temperature change characteristic and unsteady heat transfer characteristics of solid bodies previously determined in consideration of the heat transfer resistance of the interfaces. The present invention is suitable for the measurement of extensive materials, metallic materials to heat insulating materials, specifically suitable for the measurement of materials of high thermal conductivity and heterogeneous or anisotropic and is capable of accurately measuring the thermal conductivity without any special consideration on the interface heat transfer resistance at the measurement stage.

6 Claims, 10 Drawing Sheets

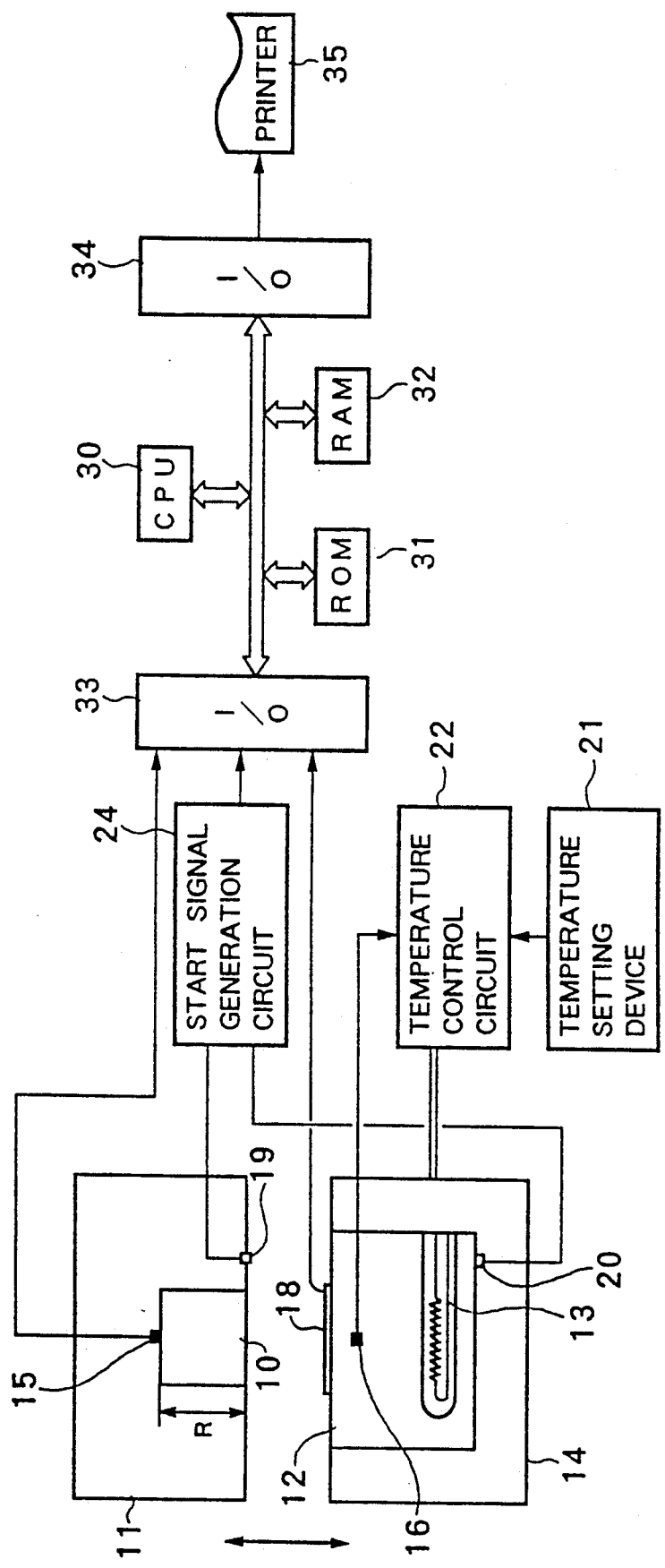

METHOD OF AND APPARATUS FOR MEASURING THERMAL CONDUCTIVITY

FIELD OF THE INVENTION AND RELATED ART STATEMENT

This invention relates to a simple and easy method of measuring the thermal conductivity of a material, and a measuring apparatus based on the method.

For use of a material, it is important to know thermal properties (specific heat, thermal conductivity, thermal diffusivity, and so on) of the material.

Conventional methods of the thermal conductivity measurement are grouped into stead-state methods and unsteady-state methods. A steady-state method resides in effecting measurement when the heat flow in a material reaches a steady state. In this method, the measurement cannot be made unless a stable steady state is established, and the time for the measurement is necessarily long. An unsteady-state method resides in a process of producing a change in the temperature of a certain portion of a material, examining the propagation of this change to another portion, and calculating thermal conductivity of the material on the basis of unsteady-state heat conduction characteristics of the solid materials. According to the unsteady-state method, the measurement time is ordinarily short since the thermal conductivity is calculated from the data in initial state of the temperature change. Thermal conductivity measurement based on the unsteady-state method is widely utilized at present so long as the degree of the measurement accuracy required is not particularly high. An angstrom method (periodic heating method), a laser flash method, a hot wire method (all of which are transient phenomenon methods) and so on are known as examples of conventional unsteady-state methods.

For the inventors of the present invention, there was a strong need for measuring the thermal properties of carbonaceous materials especially a carbon fiber/carbon composite material. The carbon fiber/carbon composite material has high thermal conductivity and strong thermal anisotropy and is also heterogeneous. A carbon fiber/carbon composite material made from a chop of carbon fiber robing or carbon fiber cloth is not homogeneous, because it consists of bundles of carbon fiber portions and carbon matrix portions. The material has a large anisotropy with respect to the pressing direction at the stage of molding. Also, the thermal conductivity of the carbonaceous materials greatly varies depending upon the production process specifically on the temperature at which it is heat-treated after the carbonization. Carbon fiber/carbon composite materials are produced so as to have a wide range of thermal conductivities from that of the heat insulating materials to that of the metallic materials according to their use.

Methods of efficiently measuring the thermal conductivity of materials having such thermal characteristics based on the above-mentioned unsteady-state method will be examiner below. A laser flash method is suitable for the measurement of high thermal conductivity materials but is not suitable for measuring a large anisotropy or a heterogeneous material, because the size of a specimen measured by this method is limited to a relatively small size (to at most a diameter of 8 to 10 mm or a thickness of 1 to 3 mm), and also this method requires a large scale and rather sophisticated measuring apparatus.

Recently, a hot wire method has been used widely being improved and simplified. This type of method, however, is considered to be not always suitable for measuring materials having a high thermal conductivity. For example, for a measuring apparatus for this method, an upper measurement limit is 3 to 10 (kcal/mh C°). Although some improved method or apparatus have been proposed ("About Ketherm QTM": the technical data of Kyoto Denshi Kogyo (k.k.). "Method of Measuring the Thermal Conductivity of Solid Bodies Based on the Unsteady Thin-Wire-Heating Comparison Method": the Japan Machinery Society Paper Collection), ordinarily a hot wire method entails a problem in the case of measurement of an anisotropic material.

A technique disclosed in Japan Patent Laid-Open No. 62-148845 is known as an example of the method of measuring the change in the temperature of one end surface of a specimen while maintaining the other end of the specimen in contact with a heat source maintained at a predetermined temperature. In this technique, the one end of the specimen is also brought into contact with another heat source. Thus, the technique basically belongs to the steady state method, and inevitably needs heat flux measurement. A problem of contact resistance between the heat source and the material is also encountered and the object of the measurement is therefore claimed to be limited to flat deformable materials.

As described above, there is no simple measuring method specifically suitable for measuring materials which have a high thermal conductivity (for about 50 Kcal/mh °C.) and a strong thermal anisotropy and which are heterogeneous. In consideration of these circumstances, the inventors of the present invention have examined a simple method which resides in measuring the change in the temperature of one end surface of a specimen while maintaining the other end of the specimen in contact with a heat source maintained at a predetermined temperature to determine the heat conductivity of the material from the measurement result.

The measuring method examined by the inventors of the present invention also entails the same problem of contact resistance between the heat source and the material when it is applied for the measurement of high thermal conductivity materials, and the result of the measurement varies according to the contact condition. To cope with this problem, the inventors have also examined the method of minimizing the heat transfer resistance at the interface between the heat source and the material, but have not obtained satisfactory results.

OBJECT AND SUMMARY OF INVENTION

The object of this invention is to provide a simple method and an apparatus for measuring the thermal conductivity of the material, which are suitable for heterogeneous and thermally anisotropic materials, and which are adaptable for various forms of materials, more particularly:

A first object of the present invention is to provide a method and apparatus suitable for materials having a high thermal conductivity, without any special consideration of the interface heat transfer resistance at the measurement stage.

The second object of the present invention is to provide a method and apparatus suitable for thick materials having a low thermal conductivity.

The third object of the present invention is to provide a method and apparatus suitable for thin materials, To this end, in the present invention, there is provided the method of measuring thermal conductivity which comprises: measuring a temperature change at an interface between the material and a reference material of which thermal properties are known, while one end surface of a set of the material and the reference material is contacting with a heat source maintained at a predetermined temperature; obtaining a temperature change characteristic from the result of the temperature change measurement; obtaining the thermal conductivity of the material by comparison of the temperature change characteristic and heat transfer characteristics which were previously calculated based on an unsteady heat transfer between the heat source, the material and the reference material in consideration of a heat transfer resistance at the interface. As shown in FIG. 1, FIG. 2 and FIG. 3, the measuring apparatus includes: the heat source 1 maintained at a predetermined temperature; temperature change measuring device 3 for measuring a temperature change at the interface between the material 2 and the reference material 7 of which thermal properties are known, while maintaining a set of the material 2 and the reference material 7 in contact with the heat source 1; characteristic calculating device 4 for obtaining a temperature change characteristic from the result of measurement effected by the temperature change measuring device 3; heat transfer characteristic memory device 5 for storing data on heat transfer characteristics which were previously calculated based on unsteady heat transfer between the heat source 1, the material 2 and the reference material 7 in consideration of a heat transfer resistance at the interface; comparison calculation device for determining the thermal conductivity of the material 2 by comparison of the temperature change characteristic obtained by the characteristic calculation device 4 and the heat transfer characteristic stored in the heat transfer characteristic memory device 5.

The temperature change characteristic for an unsteady-state heat transfer of a solid body immersed in a fluid having a constant temperature has long been known as the Gurney-Lurie chart. The Gurney-Lurie chart for a flat plate is determined as follows.

When a wide flat plate having a thickness 2 R at an initial temperature $t_o$ is heated or cooled abruptly immersed in a fluid having a temperature T, a quantity of the heat which transferred between the solid body and the fluid is proportional to the temperature difference between the solid surface and the fluid $(T-t_s)$. If the heat transfer coefficient at the surface is h, initial and boundary conditions are as follows:

initial conditions: $\Theta = 0, t = t_o$ boundary conditions: $r = \pm R$, $$(dQ/d\Theta)/A = q/A = h(T - t_s)$$

$\Theta$ = time $r$ = distance from the center $A$ = cross-sectional area of the flat plate The differential equation $(\delta t/\delta\Theta = \alpha(\delta^2/\delta X^2))$ of unsteady heat transfer is calculated to obtain solutions as the relationship between the following four dimensionless terms:

$X = \alpha\Theta/R^2 = (k/\rho Cp)(\Theta/R^2)$ $Y = (T-t)/(T-t_o)$ $m = k/(hR)$ $n = r/R$ $\alpha$: thermal diffusivity $k$: thermal conductivity $h$: heat transfer coefficient FIG. 4 shows a chart reported by H. C. Hottel based on the calculation for the case of n=0.

$$Y_m = (T-t_m)/(T-t_o)$$

T: temperature of the fluid $t_m$: temperature at the center of the plate $t_o$: to initial temperature of the plate In this chart, the temperature change at the center of the plate is expressed as a relation of a dimensionless temperature Y and a dimensionless time X. The heat transfer characteristic (X—LnY) (Ln; logarithmic) is expressed as a function of m. As is apparent from the above equation, m is a parameter corresponding to the heat transfer resistance 1/h at the interface.

Originally, this chart expresses the temperature change at the center of a flat late having a thickness 2R which is immersed in the fluid. Considering the case that the temperature change of one end surface of the material is measured while the other end is kept in contact with a heat source maintained at a predetermined temperature, if the measured face of the material is well insulated, the temperature change at the measured face can be assumed to be the temperature change at the center of the material.

When the heat transfer resistance at an interface between the material and the heat source can be assumed to be negligible, we can calculate the thermal diffusivity of the material directly from the temperature change at the measured face.

The inventors tried to make the thermal diffusivity measurement based on this idea, and found the result that the thermal resistance at the interface is not negligible.

On the Gurney-Lurie chart, it is noted that the heat transfer characteristics are straight for the range of X larger than 0.5, and this characteristic $(X-LnY)_{mi}$ can be expressed by a set of data, for example, $X_{1.0,mi}$ (intersection of the line with the abscissa Y=1.0) and $X_{0.5,mi}$ (X for Y=0.5 in the case of each values of mi). This notice is the base of the first embodiment of this invention.

When the temperature change at the measured face of the material is expressed by a temperature change characteristic $(\Theta - LnY)$ as shown in FIG. 5, the intersection $\Theta_{1.0}$ of this characteristic with the abscissa Y = 1.0 should correspond to the above described $X_{1.0,mi}$, and there should be the relationship:

$$\Theta_{1.0}/X_{1.0,mi} = \Theta_{0.5}/X_{0.5,mi}$$

Accordingly, the process for determining the heat transfer characteristic (X—LnY) for the one thermal resistance m is effected by a process comparing the temperature change characteristic and the heat transfer characteristics stored in a data storing means by a trial and error method.

The thermal diffusivity $\alpha$ and thermal conductivity k are determined by the following relationship:

$$\alpha = XR^2/\Theta$$

$$k = \alpha C_p \rho$$

The heat transfer coefficient at the interface h is also determined by the following relationship:

$$h = k/mR$$

Usually it is difficult to solve the differential equation of an unsteady heat transfer analytically, but the equation can be integrated easily by numerical calculation. When temperature difference in the material in the direction of thickness $\Delta R$ is $\Delta t_R$, the quantity of heat transferred in the material appeared as follows:

$$q = A(k/\Delta R)\Delta t_R \Delta \Theta$$

The quantity heat transferred through the interface having a temperature difference $\Delta t_I$ appeared as follows:

$$q = Ah\Delta t_I \Delta \Theta$$

Then the temperature rise $\Delta t$ is calculated by the following equation:

$$\Delta t = \Delta q/AC_p\rho\Delta R)$$

Unsteady state heat transfer is numerically calculated for a semi-infinite slab of which thermal diffusibility is $\alpha_1$ contacting with a constant temperature heat source covered by a plate having a thickness R of which thermal diffusibility is $\alpha_2$.

In the same way as the above calculation for the Gurney-Lurie chart, the initial and boundary conditions are as follows:

initial conditions: $\Theta = 0, t_p = T, t_s = t_o$
boundary condtions: $r = 0, t_p = T$.

$r$: distance from the interface between the plate and the heat source
  $t_p$: temperature of the plate
  $t_s$: temperature of the semi-infinite slab It is found that the exposure time which is necessary to a definite temperature change is not affected by the interface heat transfer resistance between the plate and the slab. This finding is the base of the second embodiment of this invention.

The result of the calculation is shown in FIG. 7 as the correlation of dimensionless temperature Y and dimensionless time X as the function of dimensionless thermal diffusibility $\alpha_1/\alpha_2$.

The relationship of dimensionless time $X_Y = 0.2$ or $X_Y = 0.15$ (for the temperature change $Y = 0.2$ or $Y = 0.15$) and dimensionless thermal diffusibility $\alpha_1/\alpha_2$ is read from FIG. 7 and shown in FIG. 8.

Unsteady state heat transfer is both numerically calculated for a semi-infinite slab contacting a constant temperature heat source. In this case, the initial condition and boundary conditions are as follows:

initial conditions: $\Theta = 0, t = t_o$
boundary conditions: $r = 0, (dQ/d\Theta) = h(T - t_s)A$ $r$: distance from the interface between the semi-infinite slab and the heat source The result of the temperature change at a depth of arbitrary selected r which is obtained by calculation is also given as the Gurney-Lurie chart.

The result of the calculation for the surface of the semi-infinite slab is shown in FIG. 9 as the relationship of dimensionless time X and dimensionless temperature Y as a function of various dimensionless heat transfer resistances m.

The relationship between an exposure time X for a definite temperature change $Y = 0.2$ and the dimensionless heat transfer resistance m is read from FIG. 9 and shown in FIG. 10. When the thermal resistances of the interface are negligible compared with that of the plate which is pinched between the heat source and the semi-infinite slab, this m can be considered as the thermal resistance of the plate which is expressed by $1/h = R/k_2$. There should be the following relationship:

$$m = k_1/hR = k_1/k_2$$

$k_1$: thermal conductivity of the plate $k_2$: thermal conductivity of the slab This relationship is the basis of the third embodiment of the present invention.

BRIEF DESCRIPTION OF THE DRAWINGS

FIG. 11 is a diagram of the basic construction of the measuring apparatus in accordance with the first embodiment.

DETAILED DESCRIPTION OF THE PREFERRED EMBODIMENT

Figure 1:
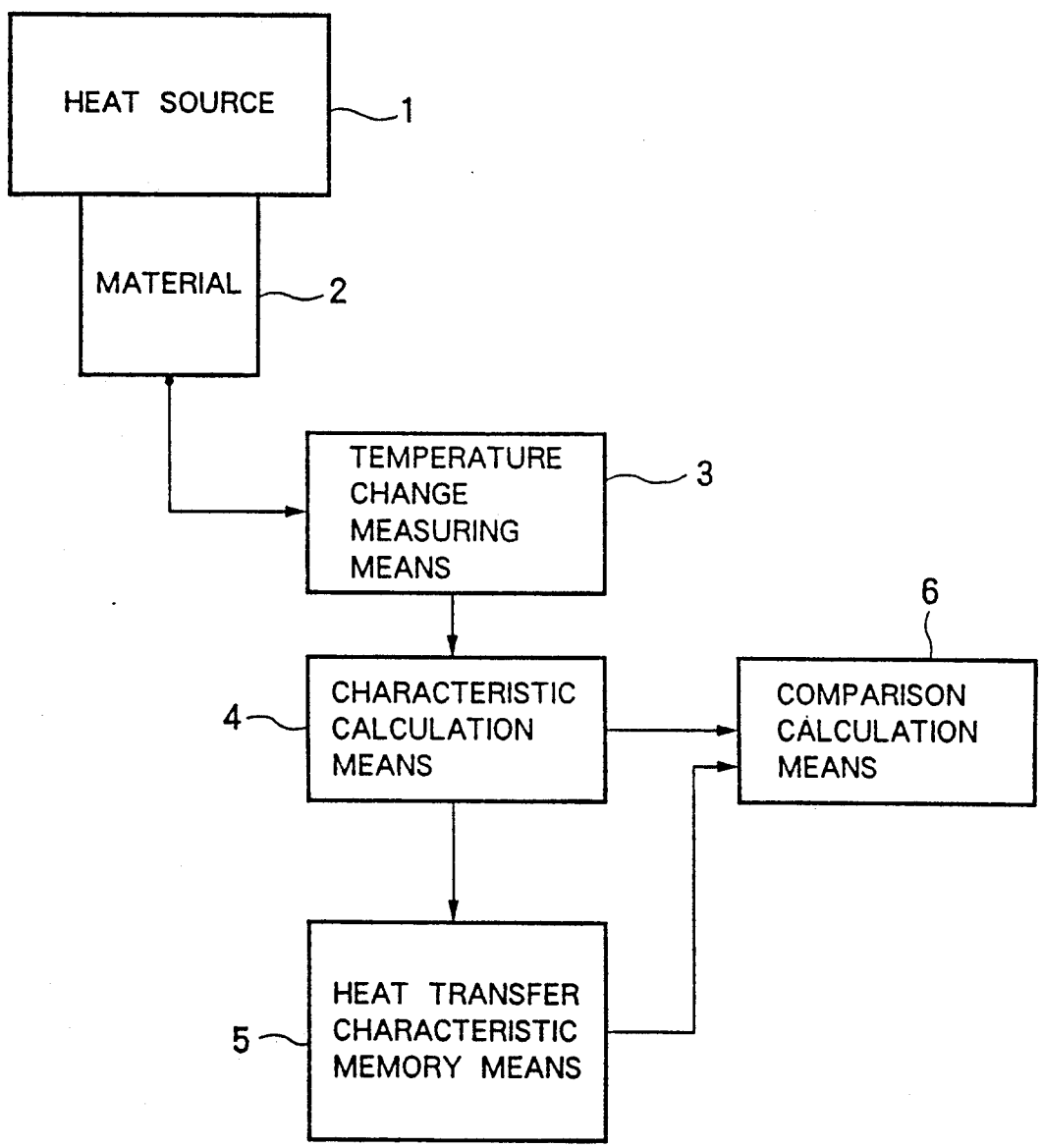
FIG. 1 is a block diagram of the construction of a measuring apparatus of the first embodiment of this invention.

The first embodiment of the present invention will be described below rather in detail with reference to the accompanying drawings.

FIG. 11 shows the basic construction of a thermal conductivity measuring apparatus in accordance with the first embodiment.

A piece of material 10 having a prism-like shape is provided as a specimen. The material piece 10 is set in a reference material 11 having a property of a heat insulator. The material piece 10 has one end surface exposed. A temperature sensor 15 such as a thermocouple is provided on a surface of the material piece opposite to the exposed surface. A metallic block 12 is heated by a heater 13 embedded in the metallic block 12 to serve as a heat source. The metallic block 12 is covered with a heat insulating member 14 in such a manner that only its surface facing the material piece 10 is exposed. A temperature sensor 16 is embedded in the metallic block along with the heater 13. The heat insulating member 11, in which the material piece 10 is set, is vertically movable and is pressed against the metallic block 12 and the insulating member 14.

When a heat capacity of the material should be determined, a heat flux sensor 18 is fixed on the exposed surface of the metallic block 12 so as to be pinched between the material piece 10 and the metallic block 12 while the press holding state is maintained.

The measuring apparatus has a temperature setting device 21 and a temperature control circuit 22. The temperature control circuit 22 effects on-off control of the heater 13 so that the detected temperature from the temperature sensor 16 provided in the metallic block 12 becomes equal to a temperature set by means of the temperature setting device 21. The measuring apparatus also has a start signal generation circuit 24 which outputs a start pulse when a start contact 19 provided on a surface of the heat insulating material 11 is electrically connected to another start contact 20 provided on the back surface of the metallic block 12. R represents the distance between the exposed surface and the back surface of the material piece 10.

Referring also to FIG. 11, a calculation system of this measuring apparatus has a CPU 30 for effecting various calculations and over all control of respective units, a ROM 31 in which various categories of data, programs and the like are stored, and a RAM 32 for storing the result of the calculations. The CPU 30, the ROM 31 and the RAM 32 are connected to each other by a bus. A signal from the temperature sensor 15 provided on the back surface of the material piece 10, the start pulse from the signal generation circuit 24 and a signal from the heat flux sensor 18 are respectively input into the CPU 30 through an input interface circuit 33, and data about the calculations effected by the CPU 30 is supplied to a printer 35 though a output interface 34.

Figure 4:
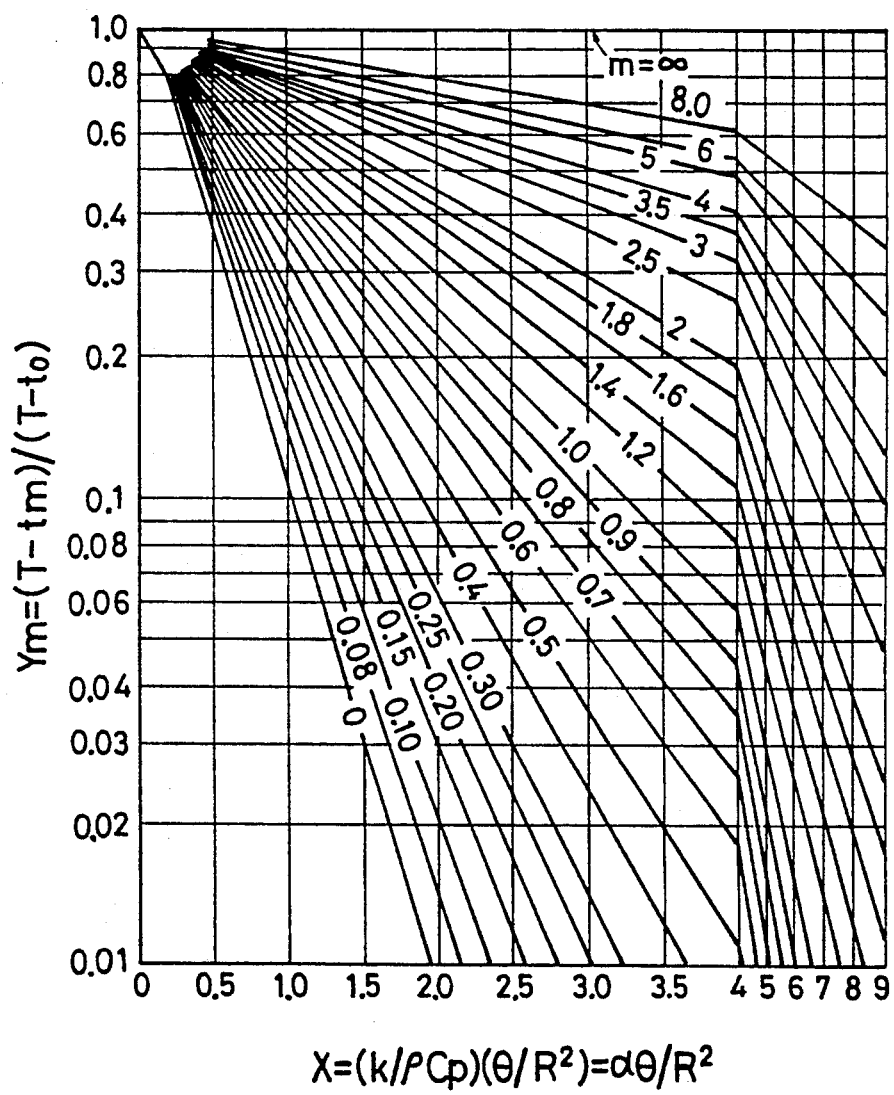
FIG. 4 is a modified Gurney-Lurie chart reported by H. C. Hottel.

Data about heat transfer characteristics expressed by a Gurney-Lurie chart such as that shown in FIG. 4 is previously stored in the ROM 31 with which a heat transfer characteristic memory means which is a constituent of the present invention is realized. A characteristic calculation means and a comparison calculation means which are other constituents of the present invention are realized as functions of the CPU 30.

The thermal conductivity of material 10 is measured with the thus-constructed measuring apparatus, as described below.

The metallic block 12 serving as a heat source is maintained at the predetermined temperature T by the control of the temperature control circuit 22. In this state, the heat insulating member 11, in which the material piece 10 is set, is held pressed against the metallic block 12. At this time, the start contacts 19 and 20 are connected and a start pulse is output from the start signal generation circuit 24. When this start pulse is output, the CPU 30 starts observing an internal timer and successively stores in the RAM 32 the signal from the temperature sensor 15 as detected temperature data $t_m$ at the predetermined times.

When a predetermined number of times of sampling of detected temperature data $t_m$ is reached, the CPU 30 calculates a temperature change characteristic based on the time data 8 and the detected temperature data $t_m$. Dimensionless temperature $Y_m$:

$$Y_m = (T - t_m)/(T - t_c)$$

Figure 5:
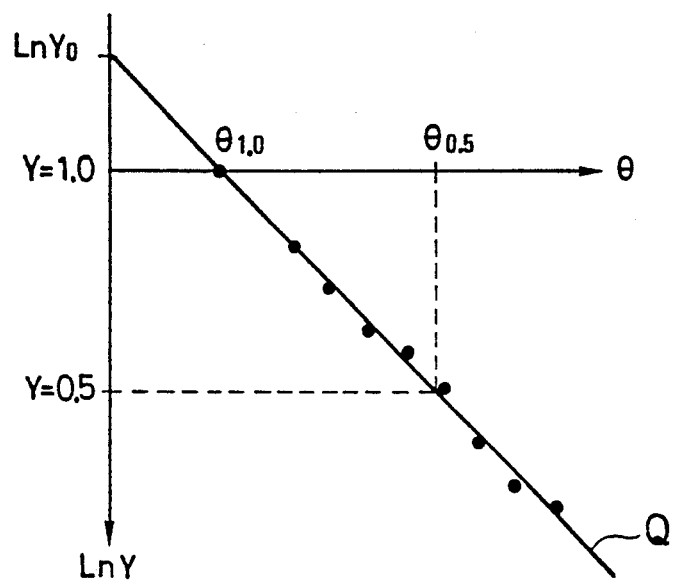
FIG. 5 is an example of a temperature chart characteristic explained in the first embodiment.

$t_o$: detected temperature data at the time of start pulse output is obtained with respect to each item of detected temperature data $t_m$ and the logarithmic value $LnY_m$ is further obtained. Then the relationship $\Theta - LnY$ is approximated to be a straight line as shown in FIG. 5:

$$LnY = a\Theta + LnY_o \qquad (1)$$

is calculated from the points $(\Theta_m, LnY_m)$ by the least squares method. After the characteristic $\Theta - LnY$ has been obtained, the thermal conductivity is obtained by comparison of the temperature change characteristic $\Theta - LnY$ and the heat transfer characteristic $X - LnY$ (refer to FIG. 4) stored in the ROM 31.

This comparison is effected as described below.

First, the heat transfer characteristic corresponding to the temperature change characteristic shown in FIG. 5 is specified as one of the straight lines.

One point on the temperature change characteristic e.g. $\Theta_{1.0}$ is calculated based on the above equation (1) for the approximated line by $$\Theta_{1.0} = -LnY_o/a$$

Also another point, e.g., $\Theta_{0.5}$ with respect to a predetermined $Y_{0.5}$ is calculated by $$\Theta_{0.5} = (LnY_{0.5} - LnY_o)/a$$

Figure 6:
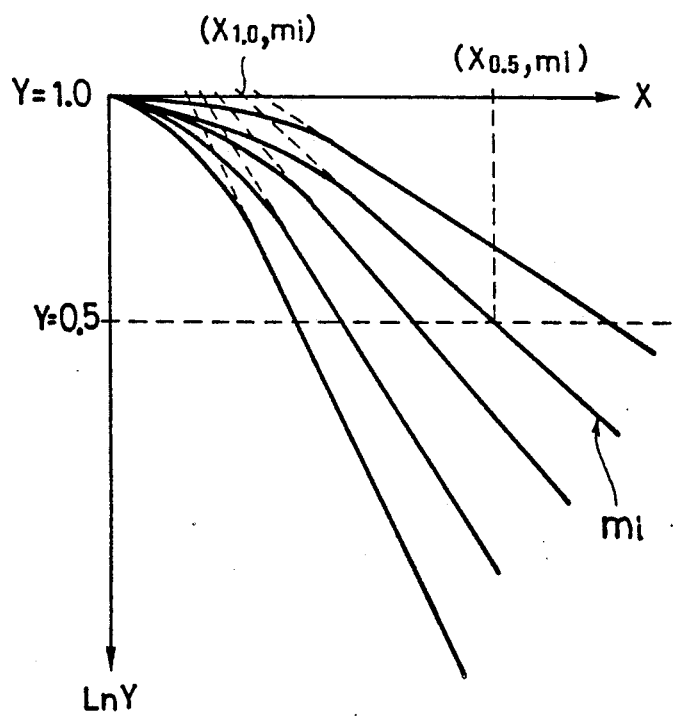
FIG. 6 is an enlarged diagram of an essential portion of the Gurney-Lurie chart shown in FIG. 4.

On the other hand, assuming that the parameter m has a value $m_i$, $X_{1.0,mi}$ of the heat transfer characteristic with respect to the parameter $m_i$ is read out, as shown in FIG. 6. This $X_{1.0,mi}$ data has previously been calculated in correspondence with the heat transfer characteristic and has been stored in the ROM 31.

This dimensionless time X of the heat transfer characteristic is proportional to the time $\Theta$, and $$X_{0.5}/\Theta_{0.5} = X_{1.0,mi}/\Theta_{1.0}$$

Therefore the $X_{0.5}$ data is calculated by $$X_{0.5} = \Theta_{0.5} X_{1.0,mi}/\Theta_{1.0}$$

using the above $\Theta_{1.0}$ and calculated $\Theta_{0.5}$. The calculated $X_{0.5}$ data and the theoretical value $X_{0.5,mi}$ calculated from the heat transfer characteristic are compared with each other. If they do not coincide, the parameter $m_i$ is slightly changed and the same calculation is successively repeated.

When the $X_{0.5}$ data coincides with the theoretical value $X_{0.5,mi}$, the heat transfer characteristic with respect to the present $m_i$ is specified as the characteristic corresponding to the measured temperature change characteristic.

After the corresponding heat transfer characteristic has been changed in this manner, the parameter $m_i$ is stored in the RAM 32, and the thermal diffusivity o is calculated from the $\Theta_{0.5}$ data and the $X_{0.5}$ data by $$\alpha = X_{0.5}R^2/\Theta_{0.5}$$

When a heat capacity of the material should be determined, the CPU 30 samples the signal from the heat flux sensor 18 by the desired timing during the above-described process, calculates the heat capacity from the value obtained by integrating the samples values until the temperature measurement is completed, and stores the value in the RAM 32.

The CPU 30 obtains the specific heat Cp and density $\rho$ from the data on the material 10 previously stored in the RAM 32, and calculates the thermal conductivity k $$k = \alpha \rho Cp$$

The heat transfer resistance 1/h is obtained by the following equation from the parameter $m_i$ specified as described above:

$$1/h = m_i R/k$$

The thermal conductivity k and other values ($m_i$, heat transfer resistance, thermal diffusivity, heat capacity), sampled temperature data and so on are read out of the RAM 32 by a command from the CPU 30 to be supplied to the printer 35. These categories of data are printed out by the printer 35 after the measurement has been completed.

Table 1 shows experimental results obtained by the measurement of the thermal diffusivity $\alpha$ of various materials performed in accordance with the above-described measuring method.

method are shown. The literature data were calculated from the known data and were shown as a reference.

In accordance with this embodiment, as described above, it is not necessary to limit the size of the specimen, average thermal conductivity with respect to the heat flow direction can be obtained even in the case of a material having a large anisotropy.

In particular, the results show that even if the thermal resistance at the interface varies, substantially the same results can be obtained. It is possible to obtain accurate data without finely controlling the state of the contact surface of the material and the heat source at the measurement stage.

The second embodiment of this invention will be described below.

Figure 2:
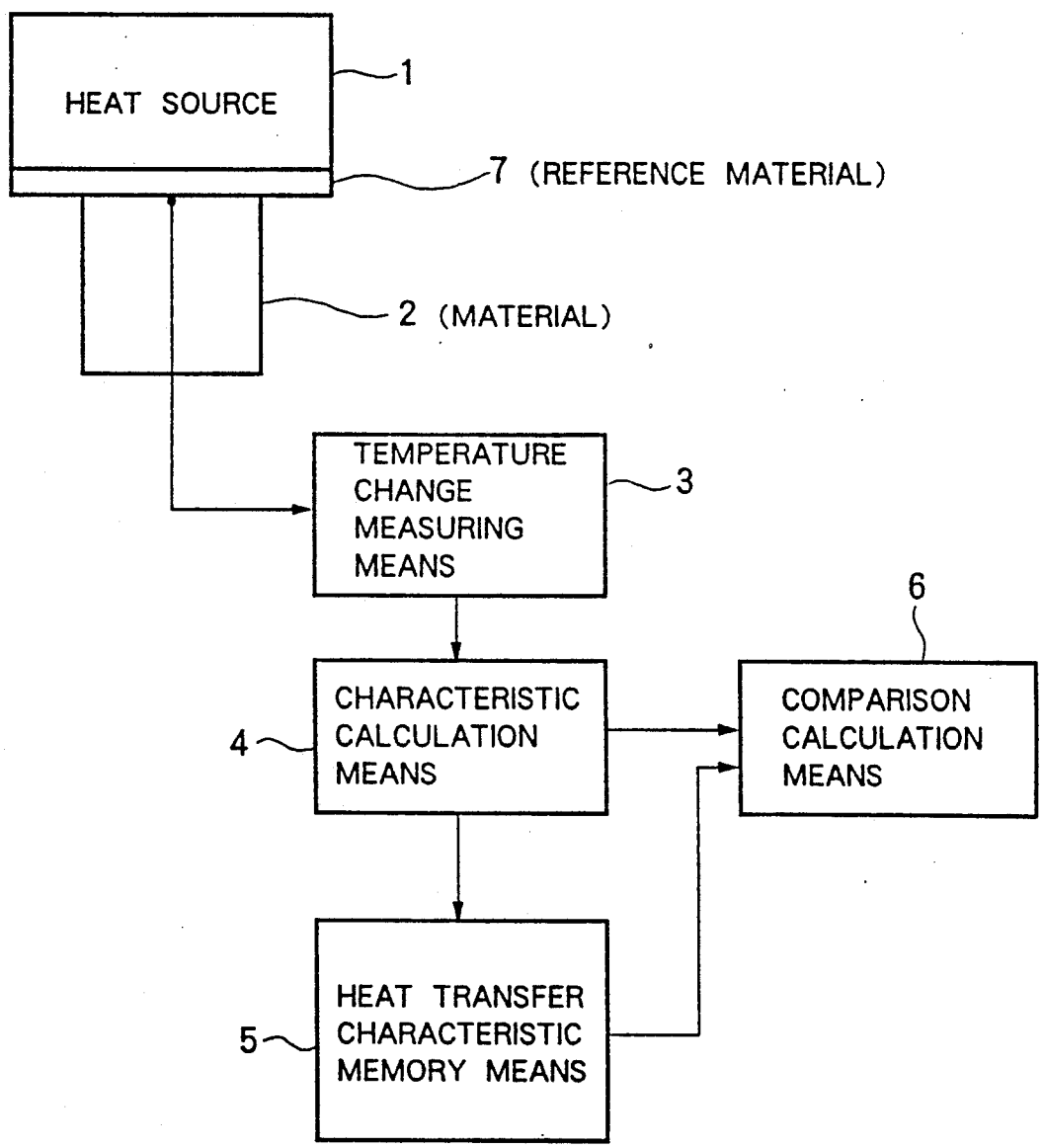
FIG. 2 is a block diagram of the construction of a measuring apparatus of the second embodiment of this invention.
Figure 7:
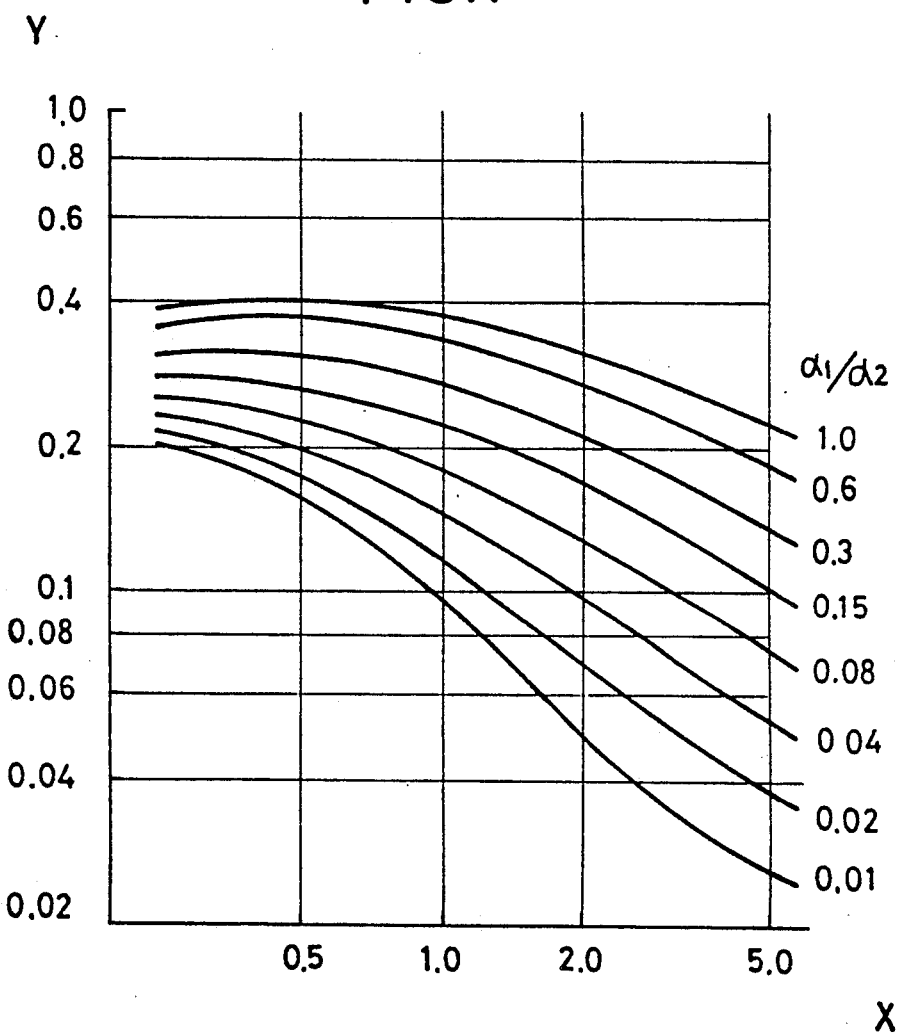
FIG. 7 and FIG. 8 are diagrams showing a relationship between X and $\alpha_1/\alpha_2$, which is used in the second embodiment.

FIG. 2 shows the arrangement of the heat source, the reference material and the material. One end surface of the material contacts with one end surface of the reference material whose other end is maintained with contact with the heat source. It is preferable that the reference material is welded or joined to the heat source so as to take away the effect of the heat transfer resistance between the heat source and the reference material. In this case the initial temperature of the reference material is the same as the temperature of the heat source. Result of the numerical calculation on the unsteady heat transfer for this arrangement is shown in FIG. 7.

When the thickness of the material is selected to be larger than 10 times that of the reference material, the range X for the reference material is less than 5.0, and the temperature change does not reach a surface of the material opposite to the contacted surface. Accordingly, the material can be assumed to be a semi infinite slab.

Figure 8:
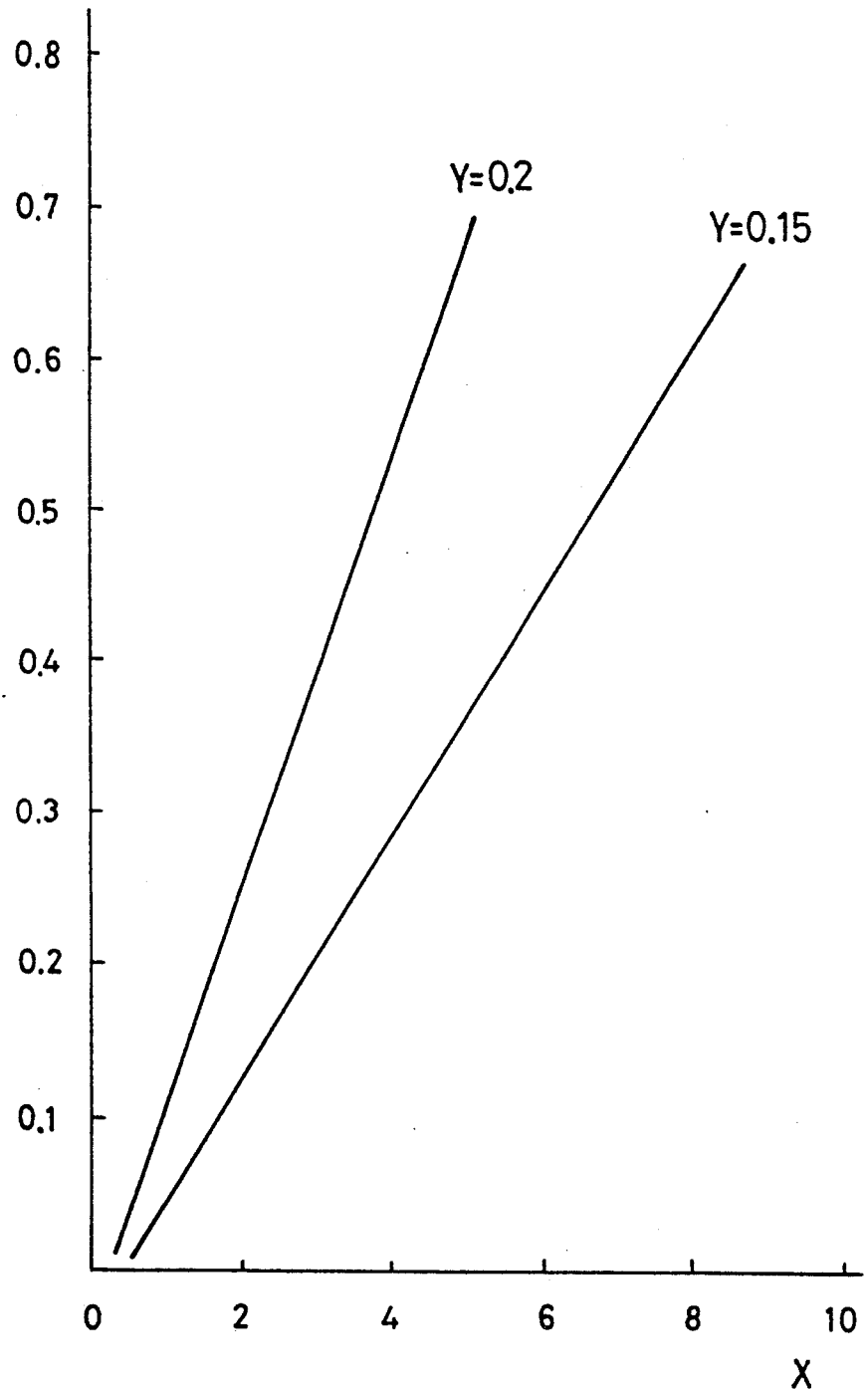

The correlation shown in FIG. 8 is used to determine the thermal diffusivity of the material.

TABLE 1

| | No. | | | | | | | | | |
|---|---|---|---|---|---|---|---|---|---|---|
| | 1 | 2 | 3 | 4 | 5 | 6 | 7 | 8 | 9 | 10 |
| | | | | | | Material | | | | |
| | | | Al | | | SS | | SUS | | Brass |
| Thickness mm | 20 | 20 | 20 | 20 | 30 | 20 | 20 | 20 | 20 | 20 |
| T °C. | 80.5 | 80.5 | 80.0 | 80.0 | 80.5 | 80.0 | 80.0 | 80.0 | 80.0 | 80.0 |
| t o °C. | 26.2 | 26.2 | 25.5 | 25.7 | 25.8 | 26.2 | 26.1 | 25.8 | 26.2 | 25.9 |
| $\theta$sec | | | | | | | | | | |
| 35° C. | | | 1.4 | 1.55 | 17.5 | 7.0 | 16.5 | 34.3 | 20.0 | 13.0 |
| 40 | 10.5 | 1.9 | 1.9 | 2.15 | 26.5 | 9.4 | 24.3 | 46.6 | 26.0 | 19.0 |
| 45 | 14.8 | | 2.3 | 2.70 | 36.8 | 11.9 | 33.2 | 60.4 | 32.8 | 26.8 |
| 50 | 19.5 | 3.1 | 2.9 | 3.30 | 49.0 | 14.9 | 44.0 | 76.5 | 40.8 | 35.0 |
| 55 | 25.3 | | 3.7 | 4.25 | 65.0 | 18.5 | 56.9 | 96.4 | 50.2 | 45.2 |
| 60 | 32.8 | 4.7 | 4.4 | 5.25 | | | | | | 58.8 |
| m | 6.15 | 0.47 | 0.39 | 0.57 | 6.77 | 0.39 | 2.16 | 0.76 | 0.24 | 4.20 |
| $\alpha$cm/sec | 0.778 | 0.782 | 0.785 | 0.778 | 0.766 | 0.152 | 0.168 | 0.041 | 0.047 | 0.314 |
| L.F. method | 0.698 | | | | | 0.100 | | 0.036 | | 0.333 |
| | 0.726 | | | | | | | | | 0.339 |
| Literature data | 0.836 | | | | | 0.148 | | 0.045 | | 0.232 |

As shown in Table 1, a plurality of parameters m are given with respect to one material; the measurements were performed under a set of conditions applying water or oil to the interface so as to change the heat transfer resistance. The results of these measurements show that generally the same thermal diffusivity $\alpha$ can be obtained irrespective of the heat transfer resistance of the interface.

In the L.F. method section of Table 1, the results of measurement of the same material based on a laser flash In this embodiment, the thermal conductivity of the material is measured as described below.

The temperature change characteristic as the relationship $\Theta - LnY$ is obtained from the result of the temperature change measurement as well as the first embodiment. The $\Theta y = 0.2$ is determined from the $\Theta - LnY$ relationship, and $Xy = 0.2$ is calculated by the below equation:

$$X_{y=0.2} = \Theta_{y=0.2}/R^2$$

Then the $\alpha_1/\alpha_2$ for the material is determined by the relationship shown in FIG. 8. Now, the thermal diffusivity $\alpha_2$ of the reference material has been known so that the thermal diffusivity $\alpha_1$ of the material can be easily determined from the value of $(\alpha_1/\alpha_2)$.

$$\alpha_1 = \alpha_2(\alpha_1/\alpha_2)$$

The third embodiment of this invention will be described below.

Figure 3:
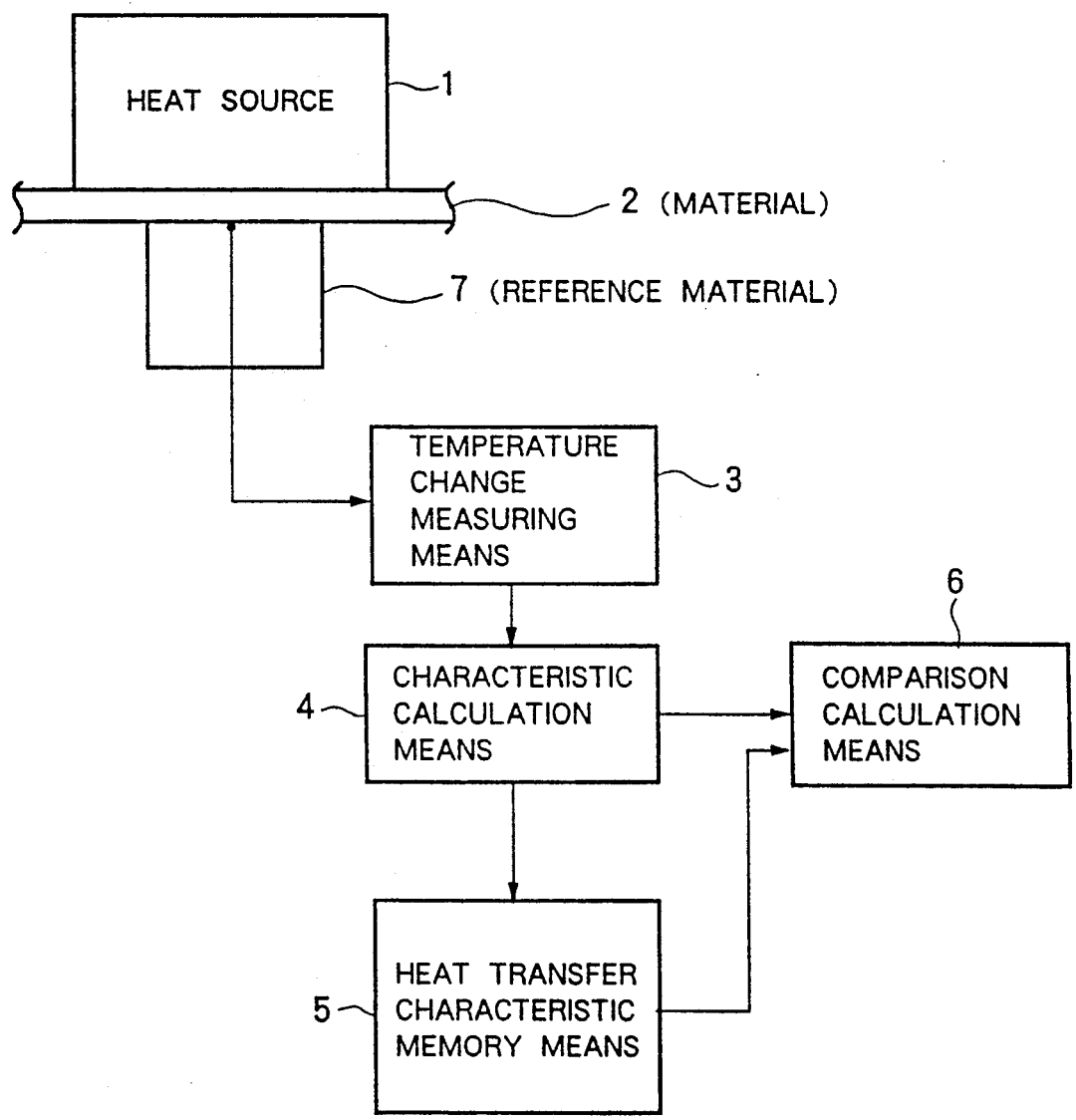
FIG. 3 is a block diagram of the construction of a measuring apparatus of the third embodiment of this invention.
Figure 9:
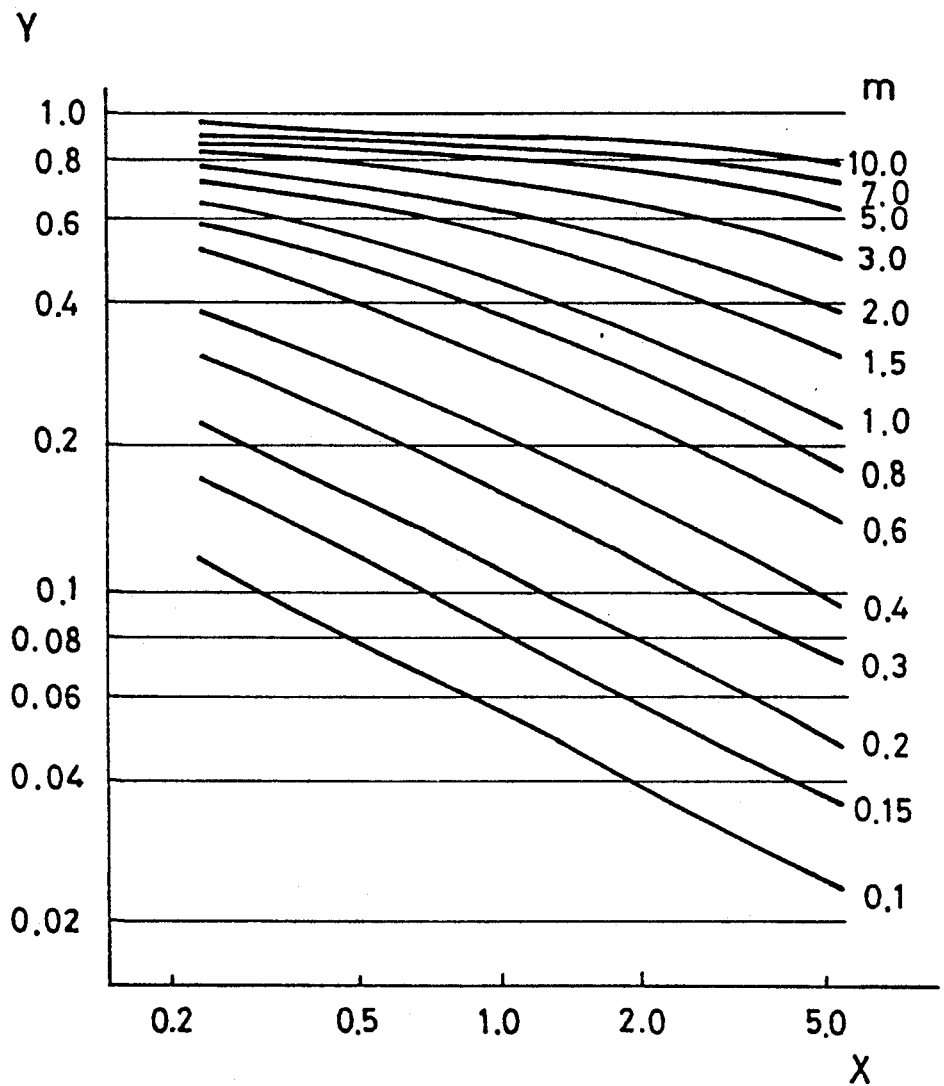
FIG. 9 and FIG. 10 are diagrams showing a relationship between X and m, which is used in the third embodiment.

FIG. 3 shows the basic arrangement of the heat source, the material and the reference material. Result of the numerical calculation for the unsteady state heat transfer on this arrangement is shown in FIG. 9. When the thickness of the material is selected to be less than 1/10 that of the reference material, for the range of X for the reference material $(X=\alpha_2\Theta/R^2)$ is less than 5.0. Accordingly, the reference material can be regarded as the semi infinite slab.

In this embodiment, the thermal conductivity of the material is measured as described below.

The temperature change characteristic is obtained from the result of the temperature change measurement as well as the first embodiment. The $\Theta_{Y=0.2}$ is determined from the $\Theta-\mathrm{Ln}Y$ relationship, and $X_{Y=0.2}$ is calculated by the below equation:

$$X_{Y=0.2} = \Theta_{Y=0.2}/R^2$$

Figure 10:
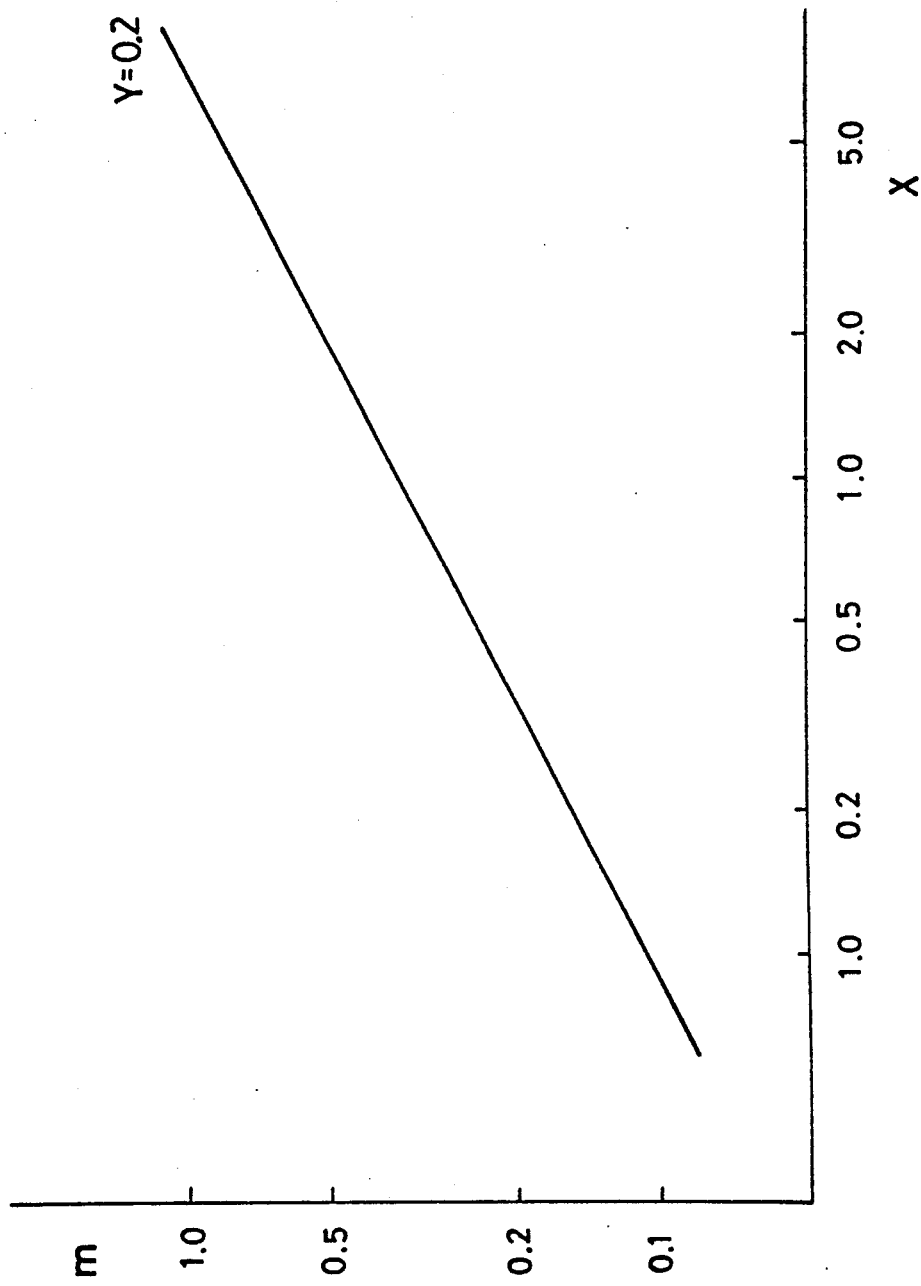

The m corresponding to the thermal resistance of the material is determined by the relationship shown in FIG. 10 using $X_{Y=0.2}$ which is calculated above.

The thermal conductivity of the material $k_1$ is calculated by $k_1 = mk_2$ $k_2$: thermal conductivity of the reference material In this calculation it is assumed that the thermal resistance of the interfaces are sufficiently small compared with the thermal resistance of the material and it can be neglected. It is preferable to make any device minimizing the interface thermal resistances. Application of a heat conductive medium such as water, alcohols, oils and silicon oils on the surfaces are suitable for the device.

What is claimed is:

1. A method of measuring thermal conductivity comprising the steps of:

placing a reference material and a material in contact with each other;

measuring a temperature change at an interface between said material and said reference material of which thermal properties are known, while one end surface of one of the material and the reference material is in contact with a heat source maintained at a predetermined temperature;

obtaining a temperature change characteristic from results of the temperature change;

obtaining the thermal conductivity of the material by comparison of predetermined temperature change characteristics and heat transfer characteristics based on unsteady heat transfer between the heat source, the material and the reference material in consideration of a heat transfer resistance at the interface.

2. A method of measuring thermal conductivity according to claim 1, wherein the material is covered on at least one side with the reference material which has a property of a heat insulator, another side surface of the material is maintained in contact with the heat source, the temperature change characteristic obtained from the results of the temperature change measurement is obtained is a linear relationship $\Theta-\mathrm{Ln}\,Y$ (Ln: logarithm) between dimensionless temperature Y:

$$Y = (T-t_m)/(T-t_o)$$

T: temperature of the heat source
$t_m$: measured temperature
$t_o$: initial temperature and time $\Theta$, and heat transfer characteristics $X-\mathrm{Ln}\,Y$ expressed by a Gurney-Lurie chart for a flat plate is used as the heat transfer characteristics in consideration of the heat transfer resistance at the interface.

3. A method of measuring thermal conductivity according to claim 1, further comprising the steps of contacting said one end surface of the material with said one end surface of said reference material, maintaining another end of said reference material in contact with the heat source, and calculating the heat transfer characteristics based on unsteady heat transfer assuming a semi-infinite slab contact by the reference material with the heat source.

4. A method of measuring thermal conductivity according to claim 1, further comprising the steps of contacting said one end surface of the material with the reference material, maintaining said another end of said material in contact with the heat source, and calculating the heat transfer characteristics based on unsteady heat transfer assuming a semi-infinite slab contact by the material with the heat source.

5. An apparatus for measuring thermal conductivity comprising:

a material;

a reference material, of known thermal properties, in contact with said material;

a heat source maintained at a predetermined temperature;

temperature change measuring means for measuring a temperature change at an interface between said material and said reference material, while maintaining one of the material and the reference material in contact with the heat source;

characteristic calculation means for obtaining a temperature change characteristic from a result of measurement by the temperature change measuring means;

heat transfer characteristic memory means for storing predetermined data about heat transfer characteristic based on unsteady heat transfer between the material and the reference material in consideration of a heat transfer resistance at the interface; and comparison calculation means for determining a thermal conductivity of the material by comparison of the temperature change characteristic, obtained by the characteristic calculation means, and the heat transfer characteristics stored in the heat transfer characteristic memory means.

6. An apparatus for measuring thermal conductivity according to claim 5, further comprising an inflow heat flux measuring means for measuring of a quantity of heat flowing from the heat source to the material, specific heat calculated from the measured quality of inflow heat used for the comparison by the comparison calculation means.

* * * * *